United States Patent [19]
Patel et al.

[11] Patent Number: 5,814,655
[45] Date of Patent: Sep. 29, 1998

[54] NON-STEROIDAL OPHTHALMIC MIXTURES

[75] Inventors: Rajesh Patel, Redwood City; Lyle M. Bowman, Pleasanton; Peng Shen, Hayward, all of Calif.

[73] Assignee: InSite Vision Incorporated, Alameda, Calif.

[21] Appl. No.: 749,020

[22] Filed: Nov. 14, 1996

[51] Int. Cl.⁶ .................. A61K 31/40; A61K 31/195; A61K 31/19

[52] U.S. Cl. .................. 514/413; 514/567; 514/570; 514/912

[58] Field of Search .................. 514/413, 567, 514/570, 912

[56] References Cited

U.S. PATENT DOCUMENTS

| | | | |
|---|---|---|---|
| 4,559,343 | 12/1985 | Han et al. | 514/264 |
| 4,829,083 | 5/1989 | Doulakas | 514/496 |
| 4,829,088 | 5/1989 | Doulakas | 514/567 |
| 4,960,799 | 10/1990 | Nagy | 514/567 |
| 5,110,493 | 5/1992 | Cherng-Chyi et al. | 514/413 |
| 5,171,566 | 12/1992 | Mizushima et al. | 424/78.04 |
| 5,192,535 | 3/1993 | Davis et al. | 424/78.04 |
| 5,296,228 | 3/1994 | Chang et al. | 424/422 |
| 5,340,572 | 8/1994 | Patel et al. | 424/78.04 |

FOREIGN PATENT DOCUMENTS

| | | |
|---|---|---|
| 2839752 | 5/1979 | Germany . |
| 58-174309 | 10/1983 | Japan . |
| 58-174310 | 10/1983 | Japan . |
| 94/10976 | 5/1994 | WIPO . |

OTHER PUBLICATIONS

Weisweiler, P.S. et al., Comparative Comfort of Flurbiprofen Solution and Indomethacin Suspension Eyedrops, J. Clinical Res. & Drug Dev. 2:223–239 (Dec. 1988).

Vulovic, N. et al. Some Studies into the Properties of Indomethacin Suspensions Intended for Ophthalmic Use, Intl. J. of Pharmaceutics 55:123–128 (Apr. 1989).

*Primary Examiner*—Zohrem Fay
*Attorney, Agent, or Firm*—Howrey & Simon

[57] ABSTRACT

Topical ophthalmic compositions for treatment of the eye are provided which comprise aqueous mixtures of a non-steroidal agent having a pKa, a pH, and a concentration of agent chosen so as to maintain at least a therapeutic amount of the agent in suspension and a therapeutic amount of the agent in solution. A method for treating diseases of the eye, including inflammation, is also provided by topically applying such aqueous mixtures to eyes in need of treatment, whereby the therapeutic amount of the drug in solution has an immediate therapeutic effect at full concentration, and the therapeutic amount of drug in suspension has a delayed therapeutic effect by release from the suspension over a period of time by reason of dissolution kinetics.

28 Claims, No Drawings

NON-STEROIDAL OPHTHALMIC MIXTURES

BACKGROUND OF THE INVENTION

1. Field of the Invention

The present invention relates to ophthalmic formulations and more particularly, ophthalmic formulations of non-steroidal agents, including non-steroidal anti-inflammatory agents.

2. Description of the Related Art

Cyclooxygenase is essential in the biosynthesis of prostaglandins which have been shown in many animal models to be mediators of intraocular inflammation. Although steroidal compounds have been used to treat such inflammation, non-steroidal anti-inflammatory agents, from of the group of drugs known as cyclooxygenase inhibitors, have been substituted for steroids because they have not shown the same propensity to produce side-effects in ocular tissues as ophthalmic steroids.

Non-steroidal agents are also widely prescribed to reduce pain and inflammation in a wide number of tissues. When used as topical agents in the eye, they suppress inflammatory responses and to prevent particular side-effects of surgical trauma (on the pupil preventing surgical meiosis), fluid accumulating in the back of the eye after cataract surgery (post-surgical macular edema) and the appearance of inflammatory cells and vessel leakage in the anterior chamber. Topical application of non-steroidal anti-inflammatory agents in the eye also appears to relieve some of the itching due to allergic conjunctivitis. Diclofenac sodium, suprofen, and flurbiprofin are non-steroidal anti-inflammatory agents that have been used for the treatment of postoperative inflammation in patients who have undergone cataract extraction.

Non-steroidal agents, including non-steroidal anti-inflammatory agents, have in the past been administered in solutions at neutral pH. Injection of non-steroidal agents in the form of a suspension has also been proposed. Suspensions have been used for topical ophthalmic applications when the agent is not very soluble. However, when the agent is soluble, at an acceptable pH, solutions are usually used to avoid potential irritation caused by the particles of a suspension. The following patents illustrate ophthalmic solutions containing various non-steroidal agents, including non-steroidal anti-inflammatory agents.

U.S. Pat. No. 4,960,799 to Nagy concerns a storage stable aqueous solution of sodium ortho-(2,6-dichlorophenyl) aminophenylacetate acid, which is the chemical name for diclofenac sodium, for topical treatment of ocular inflammation. The solution taught by Nagy has a pH of about 7.0 to 7.8.

U.S. Patent No. 4,829,083 to Doulakas relates to stabilization of mercury-containing preservatives in liquid or gel ophthalmic medicaments with addition of 2-amino-2-hydroxymethyl-1,3-propanediol or a homologue thereof.

U.S. Pat. No. 4,829,088 to Doulakas also relates to an ophthalmic medicament containing diclofenac sodium in aqueous solution. The solution contains 2-amino-2-hydroxymethyl-1,3-propanediol as a preservative.

U.S. Pat. No. 5,110,493 to Cherng-Chyi et al. relates to ophthalmic non-steroidal anti-inflammatory drug formulations containing a quaternary ammonium preservative and a non-ionic surfactant.

Generally, solubility of any non-steroidal agent depends upon several factors, including the ionic nature of the agent, the solvent system, the pH, and the temperature. The degree of solubility of the agent is directly related to its bioavailability. Thus, agent which is in solution provides an immediate therapeutic effect at full concentration, while the concentration of agent which is in suspension is provided in the eye with a more delayed therapeutic effect by reason of dissolution kinetics.

Most non-steroidal agents, including non-steroidal anti-inflammatory agents, when used in a topical solution, however, sting upon placement in the eye. The transient burning and stinging causes tearing, which in turn, washes the drug away from the eye, resulting in reduced bioavailability of the drug. The conventional solutions of non-steroidal anti-inflammatory agents generally have a pH of 7.0 to about 8.0. This pH level provides complete solubility of the drug, thereby allowing for a high concentration of the drug to be immediately available to the cornea. The high concentration of the drug on the eye, however, aggravates the burning and stinging effects of the drug when it is placed in the eye.

The present invention provides topical ophthalmic formulations containing non-steroidal agents which are partly in solution and partly in suspension, providing both immediate as well as delayed bioavailability of the drug. The topical ophthalmic formulations of the present invention thus ameliorate the burning and stinging effects of the drug when it is placed in the eye directly as a solution while providing the necessary bioavailability and desired therapeutic effect. Formulations of the present invention may be useful for treatment of any condition that may be treated by a non-steroidal agent.

The present invention also provides topical ophthalmic formulations containing non-steroidal anti-inflammatory agents which may also reduce or eliminate the stinging and burning experienced with solutions of anti-inflammatory agents while providing the necessary bioavailability and desired therapeutic effect. Formulations of the present invention may be useful for treatment of any condition that may be treated by a non-steroidal anti-inflammatory agent.

Accordingly, it is an object of the invention to provide novel topical ophthalmic formulations containing non-steroidal agents wherein a therapeutic amount of the agent is in suspension and a therapeutic amount of the agent is in solution.

It is a further object of the invention to provide a novel method of treating the eye.

SUMMARY OF THE INVENTION

One embodiment of the present invention is a topical ophthalmic composition for treatment of the eye comprising an aqueous mixture of a non-steroidal agent having a pKa in the range of about 3.5 to about 5.0, the composition having a pH less than about 6.5 and a concentration of agent chosen so as to maintain at least a therapeutic amount of the agent in suspension and a therapeutic amount of the agent in solution.

The present invention also provides a method for treating diseases of the eye, including inflammation, by topically applying such aqueous mixtures to eyes in need of treatment, whereby the therapeutic amount of the drug in solution has an immediate therapeutic effect at full concentration, and the therapeutic amount of drug in suspension has a delayed therapeutic effect by release from the suspension over a period of time by reason of dissolution kinetics.

DETAILED DESCRIPTION OF THE INVENTION

The present invention provides a composition for treating the eye topically comprising an aqueous mixture of a non-steroidal agent, wherein the agent comprises a weak acid having a pKa in the range of about 3.5 to about 5.0, preferably in the range of about 3.5 to about 4.5, the composition being formulated with a pH less than about 6.5, preferably in the range from about 6.0 to about 6.5, and a concentration of drug which maintains at least a therapeutic amount of the agent of the formulation in suspension and a therapeutic amount of the agent of the formulation in solution. The amount established in suspension may vary depending on therapeutic needs but it will be at least an amount sufficient to have a therapeutic effect on the eye upon delayed release from the suspension over a period of time. A sufficient amount of agent will also be present in solution to have an immediate therapeutic effect upon topical ophthalmic application. Typically, about 80% to about 90% of the total agent contained in the mixture will be in suspension, but this may vary depending on how much of the agent is desired for delivery and the duration of delivery desired. The amount of therapeutic agent in suspension may, for instance, range from about 70% to about 99% or about 10% to about 99% by weight of the total amount of agent contained in the mixture. The compositions will not, however, have 100% of the agent in suspension. Some amount will be in solution to provide the immediate therapeutic effect.

Compositions of the present invention may have a pH less than about 6.5, preferably in the range from about 6.0 to about 6.5, depending on the solubility characteristics of the agent. The concentration of the agent and the pH of the composition will be selected to ensure that a sufficient amount of the therapeutic agent is in suspension to provide a therapeutic effect upon delayed delivery. In this way, the portion of the agent in solution is immediately available for therapeutic effect at full concentration, while the portion in suspension serves as a reservoir and is released slowly over time.

The majority of non-steroidal agents or drugs are either weak acids or weak bases and often have more than one pKa value. Drugs that are more completely ionized are generally more soluble than drugs that are less ionized. The extent of ionization of the drug depends upon its pKa and upon the pH of the solution. When the pKa of the drug equals the pH of the solution, the ionized and unionized forms of the drug will be in equilibrium because it will be equally likely for the drug to be ionized as for the drug to be unionized.

When the drug is a weak acid, its solubility increases as the pH of the solution increases. Generally, when the pH of the solution is at least two units greater than the pKa of the compound, i.e., pH $\geq$ pKa +2, virtually all of the drug will be in its ionized form, and thus be completely solubilized.

When the drug is a weak acid with a pKa in the range of about 3.5 to about 5.0, when placed in an aqueous mixture with a pH two units greater than the pKa, the drug will be completely solubilized. However, if the pH of the aqueous mixture is less than two units greater than the pKa, the drug will be only partially ionized, wherein an amount of the drug is in suspension and an amount of the drug is in solution.

The solubility of non-steroidal anti-inflammatory agents is also pH dependent, i.e., normally the higher the pH, the higher the solubility of the drug in the formulation. For instance, below a pH of about 6.8, as in the present invention, a formulation containing 1% diclofenac sodium, has virtually all of the diclofenac in suspension. Formulating the composition such that the drug in the formulation is present partly in suspension, rather than the drug being present completely in solution, inhibits immediate contact between the drug and tissues of the eye and in that way reduces the stinging and burning sensation experienced when a solution of such drugs places all of the drug in immediate contact with the ocular tissues.

As demonstrated by Tables 1, 2 and 3, the percentage of diclofenac sodium, suprofen, and flurbiprofen in suspension is dependent on concentration and pH. Thus, by providing at least some of the diclofenac in suspension, via pH control, lower transient burning and stinging would be observed when administered to patients.

TABLE 1

Percent Diclofenac Sodium in Suspension

| pH | Concentration of Diclofenac Sodium in the Formulation | | | |
|---|---|---|---|---|
| | .001 | .01 | .1 | 1.0 |
| 3.7 | 100 | 100 | 100 | 100 |
| 4.0 | 99 | 99 | 99 | 99 |
| 4.6 | 90 | 99 | 99 | 99 |
| 5.2 | 20 | 92 | 99 | 99 |
| 5.9 | 0 | 50 | 95 | 99 |
| 6.3 | 0 | 0 | 76 | 98 |
| 6.5 | 0 | 0 | 35 | 93 |
| 7.3 | 0 | 0 | 0 | 64 |

TABLE 2

Percent Suprofen in Suspension

| pH | Concentration of Suprofen in the Formulation | | | | |
|---|---|---|---|---|---|
| | .001 | .01 | .1 | 1.0 | 5.0 |
| 4.0 | 0 | 0 | 77 | 98 | 99 |
| 5.0 | 0 | 0 | 45 | 95 | 99 |
| 6.0 | 0 | 0 | 0 | 54 | 95 |
| 7.0 | 0 | 0 | 0 | 0 | 68 |

TABLE 3

Percent Flurbiprofen in Suspension

| pH | Concentration of Flurbiprofen in the Formulation | | | | |
|---|---|---|---|---|---|
| | .001 | .01 | .1 | 1.0 | 5.0 |
| 4.0 | 20 | 92 | 99 | 99 | 99 |
| 5.0 | 0 | 33 | 93 | 99 | 99 |
| 6.0 | 0 | 0 | 0 | 80 | 98 |
| 7.0 | 0 | 0 | 0 | 24 | 92 |

The various non-steroidal agents, including non-steroidal anti-inflammatory agents, have different solubilities at a given pH. These differences in solubility are known or can be ascertained with techniques familiar to those of ordinary skill in the art. The amount of non-steroidal agent in suspension for use in the present compositions will therefore vary depending, for example, on the specific agent or drug chosen, the pKa of the drug, the dosage required, the desired release profile (the degree of sustained release), the condition for which the drug is administered and the pH of the composition. Generally, however, it is preferred to have formulations with about 70%–99% of the total non-steroidal agent in suspension although other amounts may be used (such as 10%–99%), so long as at least some of the agent is in suspension; that is an amount sufficient to have a therapeutic effect during delayed release. As previously explained, a therapeutic amount must also be in solution. The total amount of therapeutic agent, or drug, is present in the composition in an amount effective to treat the selected target condition. For inflammation of the eye, the concentration will generally be about 0.001 to about 5.0% by weight of the composition. Preferably, the drug is about 0.005 to about 3.0% by weight of the composition, and more preferably about 0.1 to about 1.0% by weight of said composition. These same ranges of drug concentrations are believed to be appropriate for treating a wide range of conditions that require therapeutic treatment as well as inflammation.

Non-steroidal agents as used herein refer to any non-steroidal agent useful for the treatment of the eyes. Preferably, the non-steroidal agent is selected from the group consisting of $N^4$ acetylsulfisoxazole, aminocaproic acid, anisindione, aspirin, bromhexine, cephalexin, chlordiazepoxide, chlorpropamide, cyproheptadine, fenprofen, furosemide, indomethacin, mefenamic acid, methanamine, metronidazole, naproxen, phenazopyridine, phenylbutazone, phenylpropanolamine, probenecid, sulfanilic acid, tetracycline, warfarin, and pharmaceutically acceptable salts thereof.

Non-steroidal anti-inflammatory agents as used herein are intended to mean any non-narcotic analgesic/nonsteroidal anti-inflammatory compound useful as a cyclooxygenase inhibitor. Preferably the non-steroidal anti-inflammatory agent is one or more of to the following: aspirin, benoxaprofen, benzofenac, bucloxic acid, butibufen, carprofen, cicloprofen, cinmetacin, clidanac, clopirac, diclofenac, etodolac, fenbufen, fenclofenac, fenclorac, fenoprofen, fentiazac, flunoxaprofen, furaprofen, flurbiprofen, furobufen, furofenac, ibuprofen, ibufenac, indomethacin, indoprofen, isoxepac, ketroprofen, lactorolac, lonazolac, metiazinic, miroprofen, naproxen, oxaprozin, oxepinac, phenacetin, pirprofen, pirazolac, protizinic acid, sulindac, suprofen, tiaprofenic acid, tolmetin, and zomepirac. Preferably, the agent is selected from the group consisting of diclofenac, suprofen, and flurbiprofen sodium and mixtures thereof. More preferably, the non-steroidal anti-inflammatory agent is diclofenac sodium.

The pKa and concentration of the non-steroidal agent in the formulation and the pH of the aqueous mixture are selected to provide sufficient drug in solution to begin effective therapeutic treatment but at least some in suspension to serve as a depot for the agent which delays release of that agent over time by reason of dissolution kinetics. The pKa of the non-steroidal agent may be in the range of about 3.5 to about 5.0. More preferably, the pKa of the non-steroidal agent is in the range of about 3.5 to about 4.5. The pH of the aqueous mixture may be less than about 6.5, and preferably in the range of about 6.0 to about 6.5, but in all cases at a level sufficient to establish the desired therapeutic amount of non-steroidal agent in suspension and the desired therapeutic amount of agent in solution.

The composition may be formulated as an aqueous mixture. The composition may contain water soluble polymers or water insoluble polymers as the suspending agent. Examples of such soluble polymers are cellulosic polymers like hydroxypropyl methylcellulose. Water insoluble polymers are preferably crosslinked carboxy-vinyl polymers. It is important to note, however, that the present invention requires the drug to be in suspension without reference to whether the polymer is or is not in suspension.

A preferred form of the invention incorporates insoluble polymers to provide a gel or liquid drops which release the drug over time. Preferably, the polymer is about 0.1 to about 6.5%, more preferably about 0.1 to about 2.0% by weight based on the total weight of the suspension of a crosslinked carboxy-containing polymer. Suitable carboxy-containing polymers for use in the present invention and method for making them are described in U.S. Pat. No. 5,192,535 to Davis et al. which is hereby incorporated by reference and relied upon. These polymer carriers include lightly crosslinked carboxy-containing polymers (such as polycarbophil, or Carbopols®), dextran, cellulose derivatives, polyethylene glycol 400 and other polymeric demulcents such as polyvinylpyrolidone, polysaccharide gels and Gelrite®. A carboxy-containing polymer system known by the tradename DuraSite®, containing polycarbophil, is a sustained release topical ophthalmic delivery system that releases the drug at a controlled rate, may also be used.

Aqueous mixtures of this invention may also contain amounts of suspended lightly crosslinked polymer particles ranging from about 0.1% to about 6.5% by weight, and preferably from about 0.5% to about 4.5% by weight, based on the total weight of the aqueous mixture. They will preferably be prepared using pure, sterile water, preferably deionized or distilled, having no physiologically or ophthalmologically harmful constituents, and will be adjusted to a pH of from about 4.0 to about 6.8, and preferably from about 5.5 to about 6.5, using any physiologically and ophthalmologically acceptable pH adjusting acids, bases or buffers, e.g., acids such as acetic, boric, citric, lactic, phosphoric, hydrochloric, or the like, bases such as sodium hydroxide, sodium phosphate, sodium borate, sodium citrate, sodium acetate, sodium lactate, THAM (trishydroxymethylaminomethane), or the like and salts and buffers such as citrate/dextrose, sodium bicarbonate, ammonium chloride and mixtures of the aforementioned acids and bases.

When formulating the aqueous mixtures, their osmotic pressure ($\pi$) may be adjusted to from about 10 milliosmolar (mOsM) to about 400 mOsM, using appropriate amounts of physiologically and ophthalmologically acceptable salts. Sodium chloride is preferred to approximate physiologic fluid, and amounts of sodium chloride ranging from about 0.01% to about 1% by weight, and preferably from about 0.05% to about 0.45% by weight, based on the total weight of the aqueous mixture, will give osmolalities within the above-stated ranges. Equivalent amounts of one or more salts made up of cations such as potassium, ammonium and the like and anions such as chloride, citrate, ascorbate, borate, phosphate, bicarbonate, sulfate, thiosulfate, bisulfate, sodium bisulfate, ammonium sulfate, and the like can also be used in addition to or instead of sodium chloride to achieve osmolalities within the above-stated ranges. Sugars like mannitol, dextrose, glucose or other polyols may be added to adjust osmolarity.

The amounts of insoluble lightly crosslinked polymer particles, the pH, and the osmotic pressure chosen from within the above-stated ranges will be correlated with each other and with the degree of crosslinking to give aqueous mixtures having viscosities ranging from about 500 to about 100,000 centipoise, and preferably from about 1,000 to about 30,000 or about 1,000 to about 20,000 centipoise, as measured at room temperature (about 25° C.) using a Brookfield Digital LVT Viscometer equipped with a number 25 spindle and a 13R small sample adapter at 12 rpm. Formulations of the present invention should have a viscosity that is suited for the selected route of administration. Viscosity up to about 30,000=drop. About 30,000 to about 100,000 centipoise is an advantageous viscosity range for ophthalmic administration in ribbon form.

When water soluble polymers are used, such as hydroxypropyl methylcellulose, the viscosity will typically be about 10 to about 400 centipoises, more typically about 10 to about 200 centipoises or about 10 to about 25 centipoises.

The composition of the present invention will ordinarily contain surfactants and, if desired, adjuvants, including additional medicaments, buffers, antioxidants, tonicity adjusters, preservatives, thickeners or viscosity modifiers, and the like. Additives in the formulation may desirably include sodium chloride, EDTA (disodium edetate), and/or BAK (benzalkonium chloride) or sorbic acid.

Non-steroidal agents, including non-steroidal anti-inflammatory agents, are non-steroidal substances used in treating or ameliorating a disease or medical condition. They include drugs intended to treat therapeutically conditions of the eye itself or the tissue surrounding the eye and drugs administered via the ophthalmic route to treat therapeutically a local condition other than that involving the eye. The ophthalmic medicaments will typically be incorporated in the topical delivery systems of this invention in therapeutically active amounts comparable to amounts administered in other dosage forms, usually in amounts ranging from about 0.001% to about 5% by weight, preferably from about 0.01% to about 5% by weight, and more preferably from about 0.1% to about 1% by weight, based on the total weight of the formulation. Thus, for example, about 0.1% to about 1.0% by weight of the non-steroidal compound can be administered to the eye in this manner.

The viscous gels that result from fluid eyedrops delivered by means of the aqueous mixtures of this invention typically have residence times in the eye ranging from about 2 to about 12 hours, e.g., from about 3 to about 6 hours. The agents contained in these drug delivery systems will be released from the gels at rates that depend on such factors as the drug itself and its physical form, the extent of drug loading and the pH of the system, as well as on any drug delivery adjuvants, such as ion exchange resins compatible with the ocular surface, which may also be present. Preferably, the aqueous mixtures provide sustained concentration of the non-steroidal anti-inflammatory agent of between $10^{-8}$ and $10^{-4}$ M, and more preferably between $10^{-7}$ and $10^{-5}$ M, in the aqueous or treated tissue of the eye for at least two hours, preferably at least three hours.

Ophthalmic mixtures of the present invention may be formulated so that they retain the same or substantially the same viscosity in the eye that they had prior to administration to the eye. Alternatively, ophthalmic mixtures of the present invention may be formulated so that there is increased gelation upon contact with tear fluid. For instance, when a formulation containing DuraSite® is administered to the eye at a lower pH, the DuraSite® system swells upon contact with tears. This gelation or increase in gelation leads to entrapment of the suspended drug particles, thereby extending the residence time of the composition in the eye. The drug is released slowly as the suspended particles dissolve over time as the solubility of the drug is higher in the tear fluid. All these events eventually lead to increased patient comfort, increase in the time the drug is in contact with the eye tissues, thereby increasing the extent of drug absorption and duration of action of the formulation in the eye.

Although described above in the context of viscous aqueous polymeric mixtures containing non-steroidal agents both in solution and in suspension, the compositions of this invention can be formulated in any other suitable manner. For example, diclofenac sodium may be dissolved and added by sterile filtration to a preparation containing sodium chloride, hydroxypropyl methyl cellulose and surfactant. This mixture may then be adjusted to the appropriate pH by known techniques, for example by the addition of sodium hydroxide. Other methods will be apparent to one skilled in the art.

In general, ophthalmic formulations suitable for topical ophthalmic administration may be formulated and administered in accordance with techniques familiar to persons skilled in the art. The finished formulations are preferably stored in opaque or brown containers to protect them from light exposure, and under an inert atmosphere. These aqueous mixtures can be packaged in preservative-free, single-dose non-reclosable containers. This permits a single dose of the medicament to be delivered to the eye as a drop or ribbon, with the container then being discarded after use. Such containers eliminate the potential for preservative-related irritation and sensitization of the corneal epithelium, as has been observed to occur particularly from ophthalmic medicaments containing mercurial preservatives. Multiple dose containers can also be used, if desired, particularly since the relatively low viscosities of the aqueous suspensions of this invention permit constant, accurate dosages to be administered dropwise to the eye as many times each day as necessary. In those mixtures where preservatives are to be included, suitable preservatives are chlorobutanol, polyquat, benzalkonium chloride, cetyl bromide, sorbic acid and the like.

In order that those skilled in the art can more fully appreciate aspects of this invention, the following Tables and examples are set forth. These examples are given solely for purposes of illustration and should not be considered as expressing limitations.

TABLE 4

| COMPONENTS | Example 1 | Example 2 | Example 3 | Example 4 | Example 5 |
|---|---|---|---|---|---|
| Diclofenac Sodium | 0.01 | 1.0 | 0.01 | 1.0 | 0.01 |
| Noveon AA-1 | — | — | 1.3 | 1.3 | 1.3 |
| Hydroxypropyl Methylcellulose | 0.2 | 0.2 | — | — | — |
| Edetate Sodium | 0.1 | 0.1 | 0.1 | 0.1 | 0.1 |
| Sodium Chloride | 0.7 | 0.7 | 0.7 | 0.7 | — |
| Mannitol | — | — | — | — | — |
| Dextrose | — | — | — | — | 2.8 |
| o-Phosphoric Acid | — | — | — | — | — |
| Sodium Borate | — | — | — | — | — |
| Pluronic F127 | 0.05 | 0.2 | 0.05 | 0.2 | 0.05 |
| Sodium Hydroxide | q.s. to pH 6 | q.s. to pH 6 | q.s. to pH 6 | q.s. to pH 6 | q.s. to pH 6 |
| Purified Water | q.s. to 100% | q.s. to 100% | q.s. to 100% | q.s. to 100% | q.s. to 100% |

| COMPONENTS | Example 6 | Example 7 | Example 8 | Example 9 | Example 10 |
|---|---|---|---|---|---|
| Diclofenac Sodium | 1.0 | 0.01 | 1.0 | 0.01 | 1.0 |
| Noveon AA-1 | 1.3 | 1.3 | 1.3 | 1.3 | 1.3 |
| Hydroxypropyl Methylcellulose | — | — | — | — | — |
| Edetate Sodium | 0.1 | 0.1 | 0.1 | 0.1 | 0.1 |
| Sodium Chloride | — | — | — | 0.5 | 0.5 |
| Mannitol | — | — | — | 1 | 1 |
| Dextrose | 2.8 | — | — | — | — |
| o-Phosphoric Acid | — | 0.5 | 0.5 | — | — |
| Sodium Borate | — | 0.5 | 0.5 | — | — |
| Pluronic F127 | 0.2 | 0.05 | 0.2 | 0.05 | 0.2 |
| Sodium Hydorxide | q.s. to pH 6 | q.s. to pH 6 | q.s. to pH 6 | q.s. to pH 6 | q.s. to pH 6 |

TABLE 4-continued

| Purified Water | q.s. to 100% | q.s. to 100% | q.s. to 100% | q.s. to 100% | q.s. to 100% |
|---|---|---|---|---|---|

TABLE 5

| COMPOSITION | Example 11 | Example 12 | Example 13 | Example 14 |
|---|---|---|---|---|
| Suprofen | 1.0 | 2.0 | — | — |
| Flurbiprofen Sodium | — | — | 1.0 | 0.1 |
| Noveon AA-1 | 1.3 | 1.3 | 1.3 | 1.3 |
| Edetate Sodium | 0.1 | 0.1 | 0.1 | 0.1 |
| Sodium Chloride | 0.5 | 0.5 | 0.5 | 0.5 |
| Mannitol | 1 | 1 | 1 | 1 |
| Pluronic F127 | 0.2 | 0.05 | 0.2 | 0.05 |
| Sodium Hydroxide | q.s. to pH 6 | q.s. to pH 6 | q.s. to pH 6 | q.s. to pH 6 |
| Purified Water | q.s. to 100% | q.s. to 100% | q.s. to 100% | q.s. to 100% |

EXAMPLES 1–2

Hydroxypropylmethyl cellulose, sodium chloride, edetate sodium (EDTA), and surfactants are dissolved in a beaker containing approximately ⅓ of the final weight of water and stirred for 10 minutes with an overhead stirrer. The solution is sterilized by autoclaving at 121° C. for 20 minutes. Diclofenac sodium is dissolved separately in approximately ½ of the final weight of water and added by sterile filtration (0.22 μm filter) and stirred for 10 minutes to form a mixture. The mixture is adjusted to pH 6.0 with 10N sodium hydroxide, brought to final weight with water by sterile filtration and aseptically filled into unit-dose containers. The viscosity of compositions of Examples 1 and 2 will be about 10 up to about 200 centipoises, preferably about 10 to about 25 centipoises.

EXAMPLES 3–4

Noveon AA-1 is slowly dispersed into a beaker containing approximately ⅓ of the final weight of water and stirred for 1.5 hrs. with an overhead stirrer. Noveon AA-1 is an acrylic acid polymer available from B.F. Goodrich. Edetate sodium (EDTA) and sodium chloride are then added to the polymer solution and stirred for 10 minutes after each addition. The polymer suspension is at a pH of about 3.0–3.5. The mixture is sterilized by autoclaving at 121° C. for 20 minutes. Diclofenac sodium is dissolved separately in approximately ½ of the final weight of water, added to the polymer mixture by sterile filtration (0.22 μm filter) and stirred for 10 minutes. The mixture is adjusted to pH 6.0 with 10N sodium hydroxide, brought to final weight with water and surfactant by sterile filtration and aseptically filled into unit-dose containers.

EXAMPLE 5–6

Noveon AA-1 is slowly dispersed into a beaker containing approximately ⅓ of the final weight of water and stirred for 1.5 hrs. with an overhead stirrer. Noveon AA-1 is an acrylic acid polymer available from B.F. Goodrich. Edetate sodium (EDTA) is then added to the polymer suspension and stirred for 10 minutes. The polymer suspension is at a pH of about 3.0–3.5. The mixture is sterilized by autoclaving at 121° C. for 20 minutes. Dextrose is dissolved in ¹⁄₁₀ of the final weight of water and sterile filtered (0.22 μm filter) in to the polymer suspension and stirred for 10 minutes. Diclofenac sodium is dissolved separately in approximately ½ of the final weight of water, added to the polymer mixture by sterile filtration and stirred for 10 minutes. The mixture is adjusted to pH 6.0 with 10N sodium hydroxide, brought to final weight with water by sterile filtration and aseptically filled into unit-dose containers.

EXAMPLES 7–8

Noveon AA-1 is slowly dispersed into a beaker containing approximately ⅓ of the final weight of water and stirred for 1.5 hrs. with an overhead stirrer. Noveon AA-1 is an acrylic acid polymer available from B.F. Goodrich. Edetate sodium (EDTA), o-phosphoric acid, and sodium borate are then added to the polymer suspension and stirred for 10 minutes after each addition. The polymer solution is at a pH of about 3.0–3.5. The mixture is sterilized by autoclaving at 121° for 20 minutes. Diclofenac sodium is dissolved separately in approximately ½ of the final weight of water, added to the polymer mixture by sterile filtration (0.22 μm filter) and stirred for 10 minutes. The mixture is adjusted to pH 6.0 with 10N sodium hydroxide, brought to final weight with water and surfactant by sterile filtration and aseptically filled into unit-dose containers.

EXAMPLES 9–10

Noveon AA-1 is slowly dispersed into a beaker containing approximately ⅓ of the final weight of water and stirred for 1.5 hrs. with an overhead stirrer. Noveon AA-1 is an acrylic acid polymer available from B.F. Goodrich. Edetate sodium (EDTA), sodium chloride and mannitol are then added to the polymer suspension and stirred for 10 minutes after each addition. The polymer solution is at a pH of about 3.0–3.5. The mixture is sterilized by autoclaving at 121° for 20 minutes. Diclofenac sodium is dissolved separately in approximately ½ of the final weight of water, added to the polymer mixture by sterile filtration (0.22 μm filter) and stirred for 10 minutes. The mixture is adjusted to pH 6.0 with 10N sodium hydroxide, brought to final weight with water and surfactant by sterile filtration and aseptically filled into unit-dose containers.

EXAMPLES 11–14

Noveon AA-1 is slowly dispersed into a beaker containing approximately ⅓ of the final weight of water and stirred for 1.5 hrs. with an overhead stirrer. Noveon AA-1 is an acrylic acid polymer available from B.F. Goodrich. Edetate sodium (EDTA), sodium chloride and mannitol are then added to the polymer suspension and stirred for 10 minutes after each addition. The polymer solution is at a pH of about 3.0–3.5. The mixture is sterilized by autoclaving at 121° for 20 minutes. Suprofen or Flurbiprofen sodium is dissolved separately in approximately ½ of the final weight of water and the pH is adjusted to 7–8 with sodium hydroxide and it is then added to the polymer mixture by sterile filtration (0.22 μm filter) and stirred for 10 minutes. The mixture is adjusted to pH 6.0 with 10N sodium hydroxide, brought to final weight with water and surfactant by sterile filtration and aseptically filled into unit-dose containers.

The above discussion of this invention is directed primarily to preferred embodiments and practices thereof. It will be readily apparent to those skilled in the art that further changes and modifications in actual implementation of the concepts described herein can easily be made or may be learned by practice of the invention, without departing from the spirit and scope of the invention as defined by the following claims.

We claim:

1. A composition for topical ophthalmic application comprising: an aqueous mixture of a non-steroidal, pharmaceutical agent, said agent being a weak acid having a pKa in the range of about 3.5 to about 5.0, said composition being formulated with a pH less than about 6.5 and a concentration of agent which maintains at least a therapeutic amount of the agent of the formulation in suspension and a therapeutic amount of the agent of the formulation in solution.

2. A composition as recited in claim 1, wherein said agent is selected from the group consisting of $N^4$ acetylsulfisoxazole, aminocaproic acid, anisindione, aspirin, bromhexine, cephalexin, chlordiazepoxide, chlorpropamide, cyproheptadine, fenprofen, furosemide, indomethacin, mefenamic acid, methanamine, metronidazole, naproxen, phenazopyridine, phenylbutazone, phenylpropanolamine, probenecid, sulfanilic acid, tetracycline, warfarin, and pharmaceutically acceptable salts thereof.

3. A composition as recited in claim 1 wherein the pH is in the range of about 6.0 to about 6.5.

4. A composition as recited in claim 2 wherein the pKa is in the range of about 3.5 to about 4.5.

5. A composition as recited in claim 4 wherein the agent is about 0.01 to about 5% by weight of said composition and about 70%–99% of said agent is in suspension.

6. A composition as recited in claim 1 wherein said composition further comprises a polymer suspending agent.

7. A composition as recited in claim 6 wherein said polymer is water soluble and the viscosity of said composition is about 10 to about 400 centipoises.

8. A composition as recited in claim 6 wherein said polymer is water insoluble.

9. A composition as recited in claim 8 wherein said polymer is a lightly crosslinked carboxy-containing polymer.

10. A composition as recited in claim 9 wherein the viscosity of the composition is about 500 to about 100,000 centipoises.

11. A composition for topical treatment of the eye comprising: an aqueous suspension of a non-steroidal, pharmaceutical agent, said agent being a weak acid having a pKa in the range of about 3.5 to about 5.0, said composition having a pH less than about 6.5 and containing from about 0.1% to about 6.5% by weight based on the total weight of the suspension of a cross-linked carboxyl-containing polymer, and wherein a therapeutic amount of about 10%–99% of said agent is in suspension and a therapeutic amount of said agent is in solution.

12. A composition as recited in claim 11, wherein said agent is selected from the group consisting of $N^4$ acetylsulfisoxazole, aminocaproic acid, anisindione, aspirin, bromhexine, cephalexin, chlordiazepoxide, chlorpropamide, cyproheptadine, fenprofen, furosemide, indomethacin, mefenamic acid, methanamine, metronidazole, naproxen, phenazopyridine, phenylbutazone, phenylpropanolamine, probenecid, sulfanilic acid, tetracycline, warfarin, and pharmaceutically acceptable salts thereof.

13. A composition as recited in claim 11 wherein the pH is in the range of about 6.0 to about 6.5.

14. A composition as recited in claim 12 wherein the pKa is in the range of about 3.5 to about 4.5.

15. A composition as recited in claim 14 wherein said agent is about 0.01 to about 5% by weight of the composition.

16. A composition as recited in claim 11 wherein said polymer is about 0.1 to about 2.0% by weight of the suspension.

17. A composition as recited in claim 11 wherein the viscosity of the composition is about 1,000 to about 30,000 centipoises.

18. A composition as recited in claim 17 wherein the viscosity of the composition is about 1,000 to about 20,000 centipoises.

19. A method for treating the eye comprising: topically applying to an eye an aqueous mixture of a non-steroidal pharmaceutical agent, said agent being a weak acid having a pKa in the range of about 3.5 to about 5.0, said mixture formulated with a pH less than about 6.5 and a concentration of drug which maintains at least a therapeutic amount of the agent in suspension and a therapeutic amount of the agent of the formulation in solution, whereby the therapeutic amount of the agent in solution has an immediate therapeutic effect, and the therapeutic amount of agent in suspension has a therapeutic effect by release from the suspension over a period of time.

20. A method as recited in claim 19 wherein said agent is selected from the group consisting of $N^4$ acetylsulfisoxazole, aminocaproic acid, anisindione, aspirin, bromhexine, cephalexin, chlordiazepoxide, chlorpropamide, cyproheptadine, fenprofen, furosemide, indomethacin, mefenamic acid, methanamine, metronidazole, naproxen, phenazopyridine, phenylbutazone, phenylpropanolamine, probenecid, sulfanilic acid, tetracycline, warfarin, and pharmaceutically acceptable salts thereof.

21. A method as recited in claim 19 wherein the pH is in the range of 6.0 to about 6.5.

22. A method as recited in claim 20 wherein the pKa is in the range of about 3.5 to about 5.0.

23. A method as recited in claim 19 wherein the agent is about 0.01 to about 5% by weight of said composition and about 70%–99% of said agent is in suspension.

24. A method as recited in claim 19 wherein said aqueous mixture further comprises a polymer suspending agent.

25. A method as recited in claim 24 wherein said polymer is water soluble and the viscosity of said aqueous mixture is about 10 to about 400 centipoises.

26. A method as recited in claim 24 wherein said polymer is water insoluble.

27. A method as recited in claim 26 wherein said polymer is a lightly crosslinked carboxy-containing polymer.

28. A method as recited in claim 27 wherein the viscosity of the aqueous mixture is about 500 to about 100,000 centipoises.

* * * * *